United States Patent [19]

Evers

[11] Patent Number: 4,913,881
[45] Date of Patent: Apr. 3, 1990

[54] DOSIMETER

[75] Inventor: Wolfgang Evers, Lübeck, Fed. Rep. of Germany

[73] Assignee: Drägerwerk Aktiengesellschaft, Lübeck, Fed. Rep. of Germany

[21] Appl. No.: 257,088

[22] Filed: Oct. 13, 1988

[30] Foreign Application Priority Data

Oct. 17, 1987 [DE] Fed. Rep. of Germany ....... 3735176

[51] Int. Cl.⁴ ..................... G01N 21/27; G01N 31/22
[52] U.S. Cl. ..................... 422/56; 356/402;
356/406; 356/425; 356/446; 356/447; 364/525;
364/526; 422/58; 422/86; 422/88; 422/91;
436/167; 436/169; 436/902
[58] Field of Search ............ 422/56, 58, 83, 86,
422/88, 91, 119; 436/165, 167, 169, 902;
356/402, 406, 425, 446, 447; 364/525, 526

[56] References Cited

U.S. PATENT DOCUMENTS

| 3,276,004 | 9/1966 | Mayo | 356/402 X |
|---|---|---|---|
| 3,482,944 | 12/1969 | Plantz et al. | 422/87 |
| 3,681,027 | 8/1972 | Smith | 436/117 |
| 3,985,017 | 10/1976 | Goldsmith | 422/83 X |
| 4,592,893 | 6/1986 | Poppe et al. | 422/56 |
| 4,617,277 | 10/1986 | Bohl | 364/525 X |
| 4,678,338 | 7/1987 | Kitta et al. | 356/402 |

FOREIGN PATENT DOCUMENTS

| 0092101 | 10/1983 | European Pat. Off. | 436/902 |
|---|---|---|---|
| 0120231 | 10/1984 | European Pat. Off. | 422/83 |
| 2615375 | 10/1976 | Fed. Rep. of Germany . | |
| 59-60325 | 4/1984 | Japan | 356/406 |

Primary Examiner—Barry S. Richman
Assistant Examiner—Jill Johnston
Attorney, Agent, or Firm—Walter Ottesen

[57] ABSTRACT

The invention relates to a dosimeter wherein the substances to be detected color a chemical sensor layer. The degree of coloration of the chemical sensor layer is measured by a photometric diffusion-reflectance measuring device. This dosimeter is improved with respect to a measurement occurring during the time that the contaminant substance is effective. The foregoing is accomplished with the dosimeter of the invention in that the dosimeter has a measuring chamber which receives a diffusion element and with a light impermeable wall portion which closes off the diffusion element while at the same time being permeable to the substance to be detected. A light source and a photosensor are arranged in the measuring chamber.

10 Claims, 1 Drawing Sheet

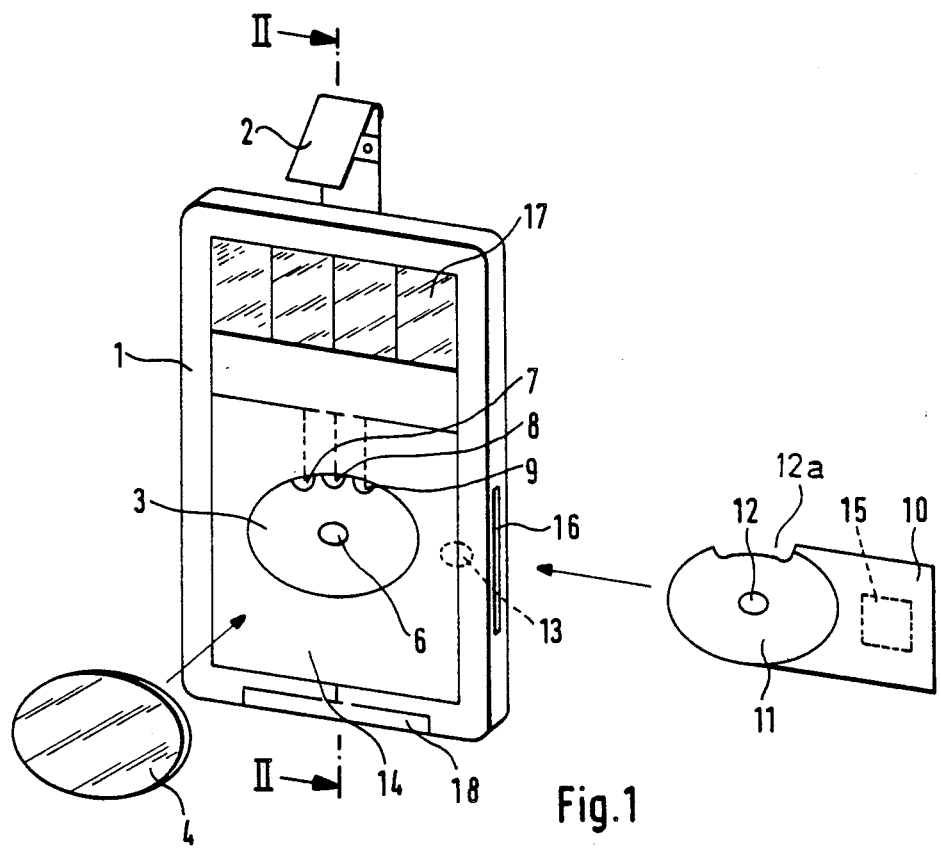
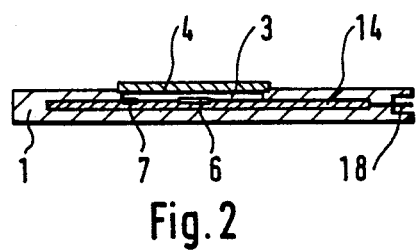
Fig.1
Fig.2

DOSIMETER

FIELD OF THE INVENTION

The invention relates to a dosimeter wherein the substances to be detected bring about the coloration of a chemical sensor layer configured as a replaceable diffusion element. The degree of coloration is measured by means of a photometric diffusion-reflectance measuring device.

BACKGROUND OF THE INVENTION

U.S. Pat. Nos. 3,482,944 and 3,681,027 disclose dosimeters worn on the apparel of persons. These dosimeters have a visual read-out of the coloration of a replaceable diffusion strip. The diffusion strip is disposed in a flat box-like housing and has a chemical sensor layer. The color changes are visually evaluated in a stepwise manner by means of a comparison with color standard zones.

U.S. Pat. No. 3,920,402 discloses a sensing element of a photocolorimetric gas analyzer with the sensing element being configured so as to be impermeable to gas. This sensing element is located in a housing and the gas mixture to be analyzed is directed in intervals over the surface which is renewed each time. The radiation reflected from the surface of the sensing element is taken up by a radiation receiver and is utilized to determine the desired measuring value.

A monitoring apparatus is disclosed in German published patent application DE-OS No. 2,615,375 wherein the replaceable diffusion element is configured as a tape and, if desired, the monitoring apparatus can be provided with a built-in optical evaluation instrument. In addition, alarm systems can be connected which can be visually noticed or emit sound in order to indicate when a critical level of toxic gas in the atmosphere has been reached or is being approached.

SUMMARY OF THE INVENTION

It is an object of the invention to provide a dosimeter which can be selectively equipped with different diffusion elements so that a continuous measurement of contaminant values is provided even during a continued exposure to the contaminant.

The object described above is achieved in a dosimeter of the kind described above by providing a measuring chamber which receives the diffusion element and which is closed off by a wall portion which is non-transparent to light but yet is permeable to the substance to be detected. In addition, a light source and a photosensor are arranged in the measuring chamber. A dosimeter of this kind is preferably arranged in a flat housing which can be easily clipped to the apparel of the wearer. This dosimeter allows for a continuous penetration of the substance to be detected through the permeable wall portion with the change in the degree of coloration occurring in the measuring chamber by means of the conversion of the chemical sensor layer. This change in the degree of coloration can be continuously measured, preferably at intervals, by means of a diffusion-reflectance measuring device which is provided with an appropriate concentration of the substance.

The photosensor is preferably mounted in the measuring chamber such that it receives essentially only scattered light reflected onto the diffusion element while the direct incidence of light from the light source is prevented. For this purpose, the photosensor can be mounted in a cutout of the diffusion element.

To prevent an incidence of light onto the photosensor which is not reflected from the sensor layer, it is advantageous to provide a light absorbing layer on the side of the permeable wall portion facing toward the measuring chamber. This light absorbing layer can be, for example, a blackened absorption layer.

The permeable wall portion is preferably a sinter metal disc which is adequately permeable for the contaminant substance to be detected.

According to a preferred embodiment of the invention, the light source comprises several light sources having different spectral ranges so that the light source which is optimal for the measuring surface of the chemical sensor layer can be selected directly by means of a code carrier connected with the diffusion element.

The measurement preferably occurs at intervals so that light pulses can be emitted in specific predetermined time intervals with the light source being configured as a flashing light source.

In an advantageous configuration of the dosimeter, the measuring circuit of the photosensor and the voltage supply circuit for the light sources can be accommodated in the housing with the current supply provided by one or more solar cells.

A further improvement can be obtained when needed by providing a chip card in the box-like housing of the dosimeter for control and signal processing. The chip card can have electronic components of the measuring circuit and voltage circuit which are exchangeable as may be required.

A further advantage is achieved in that a plug-in terminal is provided on the housing, for example, in the form of a flat plug for connection to an external read-out and programming apparatus for reading out, programming and storing the measured values.

An advantageous further embodiment is provided in that the exchangeable diffusion element is configured to have a code carrier readable into the measuring circuit.

Finally, the measuring circuit can advantageously be so configured that it includes an alarm signal element for delivering an optical and/or acoustical alarm signal when a predetermined time limit value or an alarm threshold of the harmful substance is reached.

BRIEF DESCRIPTION OF THE DRAWINGS

The invention will now be described with reference to the drawings wherein:

FIG. 1 is an isometric view of a dosimeter showing the diffusion element ready for insertion; and, FIG. 2 is a section view taken along line II—II of FIG. 1.

DESCRIPTION OF THE PREFERRED EMBODIMENTS OF THE INVENTION

FIGS. 1 and 2 show a flat housing 1 which has an attachment clip 2 for attaching the housing 1 to the apparel of a person wearing the dosimeter.

A flat cylindrically-shaped measuring chamber 3 is carved out of the housing 1 and is covered by a sinter metal disc 4. The sinter metal disc 4 covers the chamber 3 at the front wall of the housing and is shown removed therefrom in FIG. 1. A photosensor 6 is provided in the region of the bottom surface of the measuring chamber 3 and can be configured as a photodiode or a photoresistor. In the peripheral region of the measuring chamber 3, three luminous sources (7, 8, 9) are arranged as light sources which emit light in different spectral ranges, for example, red, green and blue.

The exchangeable diffusion element includes a carrier piece 10 having an appropriate paper substrate 11 impregnated as a sensor layer. A cutout 12 is carved out of the center region of the diffusion element and the photosensor 6 lies in this cutout 12 when the diffusion element is inserted into the housing 1. A cutout 12a is provided in the paper substrate 11 for accommodating the light sources (7, 8, 9).

A bar-code carrier 15 is provided on the carrier piece 10 and is readable into the measuring circuit 14 by means of a bar-code reader 13. The diffusion element 10 is introduced through a slit 16 formed in the side of the housing 1 with the bar-code carrier 15 being pushed in front of the bar-code reader 13.

The measuring circuit 14 is in the form of a chip card which is provided with electronic components. The chip card is connected with solar cells 17 for supplying voltage. Furthermore, the measuring circuit 14 is connected via appropriate connecting lines with the bar-code reader 13, the luminous sources (7, 8, 9) as well as to the flat plug 18. The flat plug 18 provides a connection to an external read-out and programming apparatus.

The diffusion-reflectance measuring device per se is built up with an electronic measuring circuit such as described in U.S. Pat. No. 3,920,402 incorporated herein by reference.

When the diffusion element is inserted, the dosimeter is switched on via an integrated microswitch (not shown) while, at the same time, the bar-code carrier 15 arranged on the rearward side of the carrier piece 10 is scanned by the bar-code reader 13. The bar-code carrier contains the following data: type of gas; calibration curve; alarm threshold; and, limit value. The corresponding read-in values are transmitted further to the measurement circuit 14.

After reading the bar code, the zero point is obtained for the unloaded chemical sensor layer by means of a short flash of the luminous source which is addressed, for example luminous source 7, and by a measurement of the diffusion reflected light. Thereafter, the measurement of the contaminant substance begins.

The gas to be measured diffuses through the light-impermeable sinter metal disc 4 into the measuring chamber 3 and colors the active surface of the chemical sensor layer on the paper substrate 11. In uniformly timed intervals of one minute, for example, the addressed luminous source flashes and irradiates the sensor layer. The light reflected from the sensor layer is detected by the photosensor 6. The measured values determined in this way are stored in a memory of the measurement circuit 14. In each instance, the last taken measured value is compared with the next to last value. If the difference of both values exceeds a predetermined desired value or if the last measured value exceeds a limit value, then an acoustical or optical alarm is provided via an alarm signal element integrated into the measurement circuit 14.

The energy supply of the measuring circuit 14 by means of the solar cells 17 can be augmented by means of rechargeable batteries. The programming of the dosimeter with respect to the type of gas, calibration, limit value, alarm threshold and the light source to be selected can also be done by means of a separate apparatus via the flat plug 18. The data can then be inputted via a keyboard. The program unit can be combined with a read-out unit to an external apparatus.

By means of the control and signal processing with the aid of the chip card, a very flat configuration is obtained.

The paper substrate 11 is impregnated with a sensor layer in dependence upon the particular gas to be detected. For example, for detecting hydrazine, the colorimetric material may be formed by an impregnation of bindone in paper substrate 11 as described in U.S. Pat. No. 3,482,944 incorporated herein by reference.

It is understood that the foregoing description is that of the preferred embodiments of the invention and that various changes and modifications may be made thereto without departing from the spirit and scope of the invention as defined in the appended claims.

What is claimed:

1. A dosimeter for detecting the presence of a substance in the form of a gas or a vapor, the dosimeter comprising:

a housing having a forward wall and a flat measuring chamber formed in said housing so as to have a rearward wall facing said forward wall;

said forward wall having a wall portion for closing said chamber to the ambient;

said wall portion being non-transparent to light and yet being permeable to said substance;

an exchangeable diffusion member adapted to be removably insertable into said measuring chamber so as to be disposed rearwardly of said wall portion and including a chemically reacting sensor layer which changes color in the presence of said substance;

said diffusion member being disposed in said chamber on said rearward wall so as to cause said sensor layer to face toward said wall portion;

said diffusion member having first and second cutouts; and, a photometric diffusion-reflectance measuring device for measuring the degree of coloration in said sensing layer, the measuring device including: light source means disposed on said rearward wall of said measuring chamber and arranged in the region of said first cutout for irradiating light onto said sensor layer; and, a photosensor also disposed in said measuring chamber on said rearward wall and mounted in the region of said second cutout for receiving the light reflected from said sensor layer.

2. The dosimeter of claim 1, said photosensor being disposed in said second cutout so as to receive only scattered light reflected on said sensor layer.

3. The dosimeter of claim 1, said wall portion being a disc made of sinter metal and having a wall surface facing toward said measuring chamber; and, a light absorbing layer disposed on said surface.

4. The dosimeter of claim 1, said light source means comprising a plurality of light sources having different spectral ranges, respectively.

5. The dosimeter of claim 1, said light source means being a flashing light source.

6. The dosimeter of claim 1, said measuring device including a measuring circuit for said photosensor and said measuring circuit being mounted in said housing; and, said light source means being mounted in said housing and including: solar cells for providing a supply current; a light source; and, a voltage supply circuit for interconnecting said light source and solar cells.

7. The dosimeter of claim 6, said housing being a flat box-like housing and said measuring circuit including a chip card having components mounted thereon, said chip card being for control and signal processing and being mounted in said housing.

8. The dosimeter of claim 7, said chip card including a plug terminal for connecting the same with an external read-out and processing apparatus.

9. The dosimeter of claim 6, said exchangeable diffusion member including a support; said sensor layer being mounted on said support; and, a read-in code carrier also mounted on said support.

10. The dosimeter of claim 6, said measuring circuit including a member for providing an alarm signal when said substance exceeds a predetermined quantity.

* * * * *